United States Patent [19]

Trossarelli

[11] Patent Number: 4,906,093
[45] Date of Patent: Mar. 6, 1990

[54] ILLUMINATOR FOR THE SPECTROSCOPIC OBSERVATION OF MINERALS, GEMS, ETC.

[75] Inventor: Carlo Trossarelli, via Lamarmora No. 22, I-10128 Turin, Italy

[73] Assignees: Paolo Roggero; Carlo Trossarelli, both of Turin, Italy

[21] Appl. No.: 222,403

[22] Filed: Jul. 21, 1988

[30] Foreign Application Priority Data

Jul. 31, 1987 [IT] Italy ................................ 67675 A/87

[51] Int. Cl.⁴ .......................... G01N 21/87; G01J 3/00
[52] U.S. Cl. ........................................ 356/30; 356/300
[58] Field of Search ........................... 356/30, 300, 319

[56] References Cited

U.S. PATENT DOCUMENTS

| | | | |
|---|---|---|---|
| 3,867,032 | 2/1975 | Bruck | 356/30 |
| 3,989,379 | 11/1976 | Eickhorst | 356/30 |
| 4,291,975 | 9/1981 | Raccah | 356/30 |

FOREIGN PATENT DOCUMENTS

| | | | |
|---|---|---|---|
| 3236817 | 4/1984 | Fed. Rep. of Germany | 356/30 |
| 87925 | 7/1980 | Japan | 356/300 |

Primary Examiner—F. L. Evans
Attorney, Agent, or Firm—Keil & Weinkauf

[57] ABSTRACT

An illuminator for the spectroscopic illumination of minerals, gems, etc., in which a substance under examination is illuminated by means of a source of white light, comprises at least one optical fiber (22) for transmitting the illumination light, passed through the substance under examination, to an observation spectroscope (30).

37 Claims, 5 Drawing Sheets

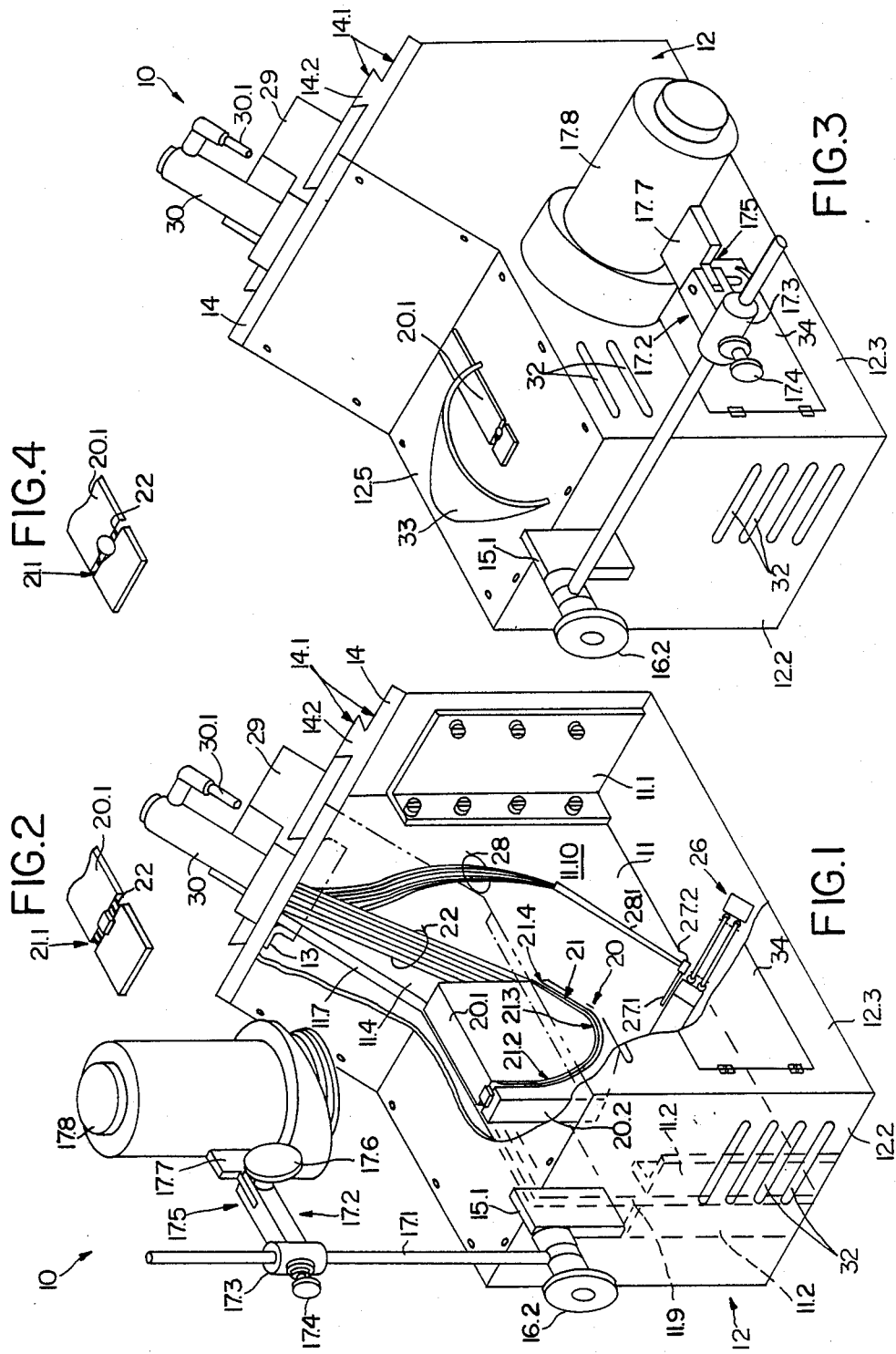

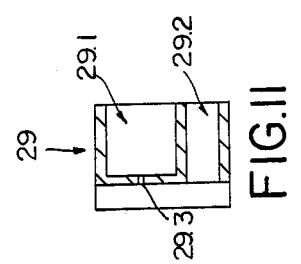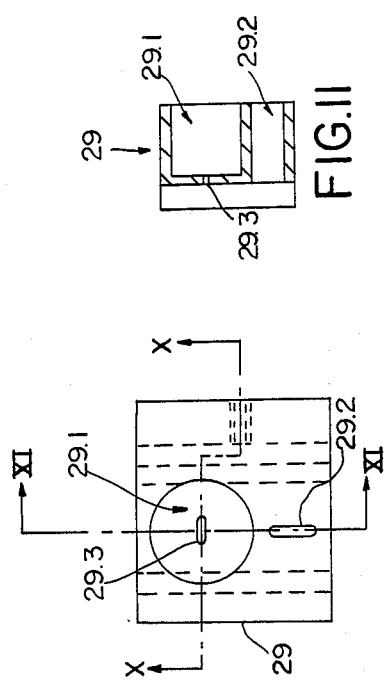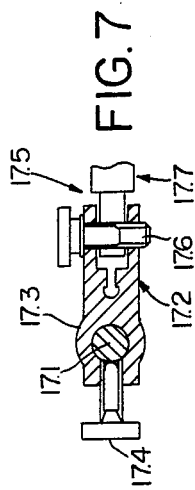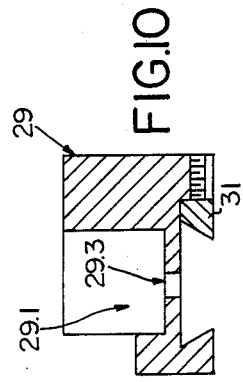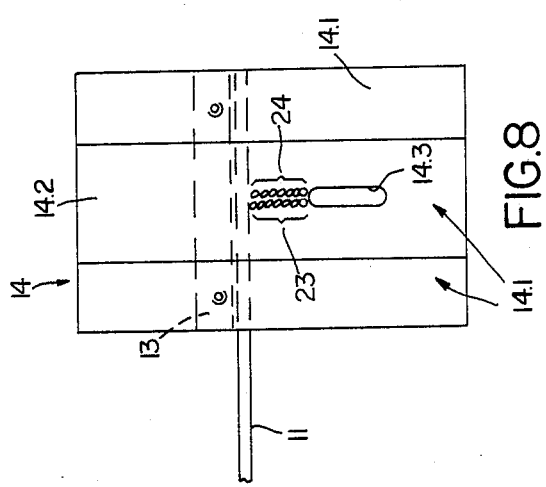

ILLUMINATOR FOR THE SPECTROSCOPIC OBSERVATION OF MINERALS, GEMS, ETC.

BACKGROUND OF THE INVENTION AND PRIOR ART

In order to optimize the illumination of a substance to be analyzed by spectroscope, there has been proposed an illuminator comprising a source of white light, such as an incandescent lamp (e.g. a halogen lamp) having a "dichroic" reflector, from which the beam of emitted/-reflected light is transmitted, through an antiheat filter and an optical system of lenses, to the input of a sheaf of glass optical fibers, the output for which is situated in the proximity of the substance to be analyzed. This illuminator is provided with a forced cooling fan device for the lamp and for the parts adjacent thereto or heated thereby through irradiation.

However, this well-known illuminator displays the following principal drawbacks:

The dichroic reflector is provided for the reflection in the direction of the sheaf of optical fibers of just radiation in the visible spectrum, and in the opposite direction, through transparency, of a certain quantity of infrared rays, responsible for the heat, thus keeping these away from the area of application of the remaining light produced by the lamp. Accordingly, a reduced quantity of heat enters the sheaf of optical fibers. However, this dichroic reflector does not limit just the infrared rays, but generates absorption lines or strips or bands, albeit faint, in the visible region of the spectrum. Furthermore, as mentioned previously, the reflector-lamp group requires a forced cooling fan device, which is, inter alia, a source of continuous and irritating noise.

The antiheat filter, provided for the purpose of keeping back through absorption the infrared rays—responsible for the heat—in the beam of light passing through the filter, offers the advantage of a partial absorption in the red and orange region starting from the commencement of the visible spectrum. These colors are in fact emitted in superabundance by incandescent lamps, and thus the filter partially "rebalances" the situation relating to the color temperature. Nonetheless, this absorption is rather greater than necessary. As a result, the residual light (i.e. the light intended for illuminating the substance) displays a dominant light green color.

The optical system of lenses entails a comparatively substantial technological and financial outlay. In the best possible case, the lenses consist of a glass, which apart from an unavoidable general absorption over the entire visible region, does not provide the residual light with a coloration that is particularly appreciable to the naked eye.

At its output, the sheaf of glass optical fibers supplies a type of light known as "cold" light (because of the actual absence of infrared rays from the emerging sheaf, rays which, as mentioned previously, are responsible for heat). In truth, this light ought to be called "unbalanced", inasmuch as it is notably lacking in blue and violet radiation, on account of a high degree of absorption in this region of the spectrum on the part of these optical fibers. Accordingly, the optical fibers in the main impart a further dominant light green color to the light transmitted by the optical fibers. In addition, from the quantity of luminous energy which these optical fibers receive from the optical system upstream, the optical fibers emit a beam of light, intended to illuminate the substance under examination, which is divergent, with a waste of energy and a reduction of the total luminous energy intended for the analysis.

It should also be noted that the human eye's sensitivity in the blue/violet region is extremely low, far more so than in comparison with the other colors of the spectrum. From this we infer the importance of the greatest possible "recovery" of energy in this region of the spectrum.

In addition to the above-mentioned drawbacks, it ought then to be borne in mind that owing to the requirements of design and construction, deriving from the principle upon which the instrument's operation is based, an exceptionally small quantity of luminous energy enters the spectroscope through a thin frontal slit. Frequently, in the use of the instrument, the shape and/or dimensions of the substance under examination are at variance with the tiny length of this slit, as shall become clearer from the following considerations relating, by way of example, to the possible types of gems et cetera to be submitted to spectroscopic analysis (for ease of exposition, the gem etc. shall hereinafter simply be referred to as "stone"):

Large stone having surfaces that are flat or rounded, but at any rate smooth; or else a large stone having relatively large facetted surfaces:

In these cases, there are no special problems inherent in observing the stone's absorption and/or emission spectrum.

Large stone having relatively small facetted surfaces:

Faces that are too small send to the spectroscope's slit bands of color having many and various directions and forms, and which, in particular, are not parallel among themselves. The observer sees a spectrum having more or less distinct patches or zones; the vision is disturbed, and any absorption or emission lines, bands or strips cannot be recognized as such; or else the limits between different unevenly illuminated zones may be mistaken for absorptions. The search for an optimal observation position becomes difficult, and may lead to unsatisfactory, contradictory or even misleading results.

Small stone:

The total light entering the spectroscope's slit consists of two separate fractions, i.e.:

a portion which has passed through the stone, and consequently having residual coloration properties governed by the nature of the stone passed through. This particular fraction is the fraction that is of use to spectroscopic analysis.

a portion reflected or transmitted by the base upon which the stone is resting, even in the event that this base is black. This portion is wholly devoid of information regarding the stone under examination.

In consequence, the observer sees a spectrum for the stone that is "diluted" in a quantity of more or less dazzling light. In this case, faint lines or bands disappear, which results in a lack of diagnostic features helpful in identifying the stone in question.

Large or small stone, and highly absorbent over the entire visible range:

stones that are highly absorbent over the entire region of the spectrum offer no opportunities for spectroscopic analysis other than at their edges (generally the thinnest edges) and/or with highly powerful illumination. In these cases we may refer to the foregoing drawback: a certain quantity of light that has not passed through the stone under examination enters the spectroscope's slit, with the same consequences as referred to above.

OBJECTS AND SUMMARY OF THE INVENTION

Accordingly, the main aim of the present invention is to provide an illuminator for the spectroscopic observation of minerals, gems et cetera, that is capable of effectively eliminating the abovementioned drawbacks.

One further aim is to provide an illuminator as specified which makes it possible to perform a simultaneous comparison of the spectra for the substance under examination with the spectra for a comparison light and/or for one or more known substances, in such a way as to be able to identify, through comparison, any absorptions or emissions which cannot be directly recognized as such, inasmuch as they are very faint, or else so as to be able to make direct comparisons of known typical spectra with the spectra for the substance under examination.

One further aim is to provide an illuminator as described which makes it possible to choose rapidly and confidently, from among several spectroscopic observation positions, that particular spectroscopic observation position in which the residual light best suited to observation is transmitted to the spectroscope.

One additional aim is to provide an illuminator as specified, one which has a simplified structure, which is safe, reliable and accurate to operate.

With these aims in mind, the present invention, briefly, provides an illuminator for the spectroscopic observation of minerals, gems, etc., in which a substance under examination is illuminated by means of a source of white light, said illuminator comprising at least one optical fiber for transmitting the residual illumination light, passed through the substance under examination, to an observation spectroscope.

BRIEF DESCRIPTION OF THE DRAWINGS

FIG. 1 is a perspective view of the entire illuminator for the spectroscopic observation of minerals, gems et cetera, in accordance with the invention, with portions in partial cutaway for reasons of clarity of illustration;

FIG. 2 is a detailed view on a larger scale, showing a substance (a stone) in the examination position in the illuminator as per FIG. 1;

FIG. 3 is a view similar to the view in FIG. 1, but showing a different operational positioning of the lamp for illuminating the substance under examination in the illuminator pursuant to the invention, in addition to an auxiliary optical reflector in the use position in the illuminator itself for the purpose of recovering luminous energy, subsequently sent on to the substance under examination;

FIG. 4 is a detailed view on a larger scale, showing a substance (a stone) in the examination position in the illuminator in accordance with FIG. 3;

FIG. 7 is a cross-sectional view according to the line VII—VII in FIG. 5;

FIG. 8 is a cross-sectional view according to the line VIII—VIII in FIG. 5, with the spectroscope-holder slide omitted for reasons of clarity of illustration;

FIG. 9 is a view of the spectroscope-holder slide for the illuminator as per the invention, in the direction of the arrow IX in FIG. 5 and with the spectroscope omitted for reasons of clarity of illustration;

FIG. 10 is a cross-sectional view according to the line X—X in FIG. 9;

FIG. 11 is a cross-sectional view according to the line XI—XI in FIG. 9.

FIG. 12 is a cross-sectional view similar to that shown in FIG. 5 except that in FIG. 12 a separate source for the emission of comparison white light has been dispensed with.

DETAILED DESCRIPTION OF THE PREFERRED EMBODIMENT

A. The Structure of the Illuminator According to the Disclosed Embodiment.

With reference to the drawings, the FIG. "10" indicates in its entirety the illuminator for the spectroscopic observation of minerals, gems et cetera, in accordance with the present invention.

Figure 5:
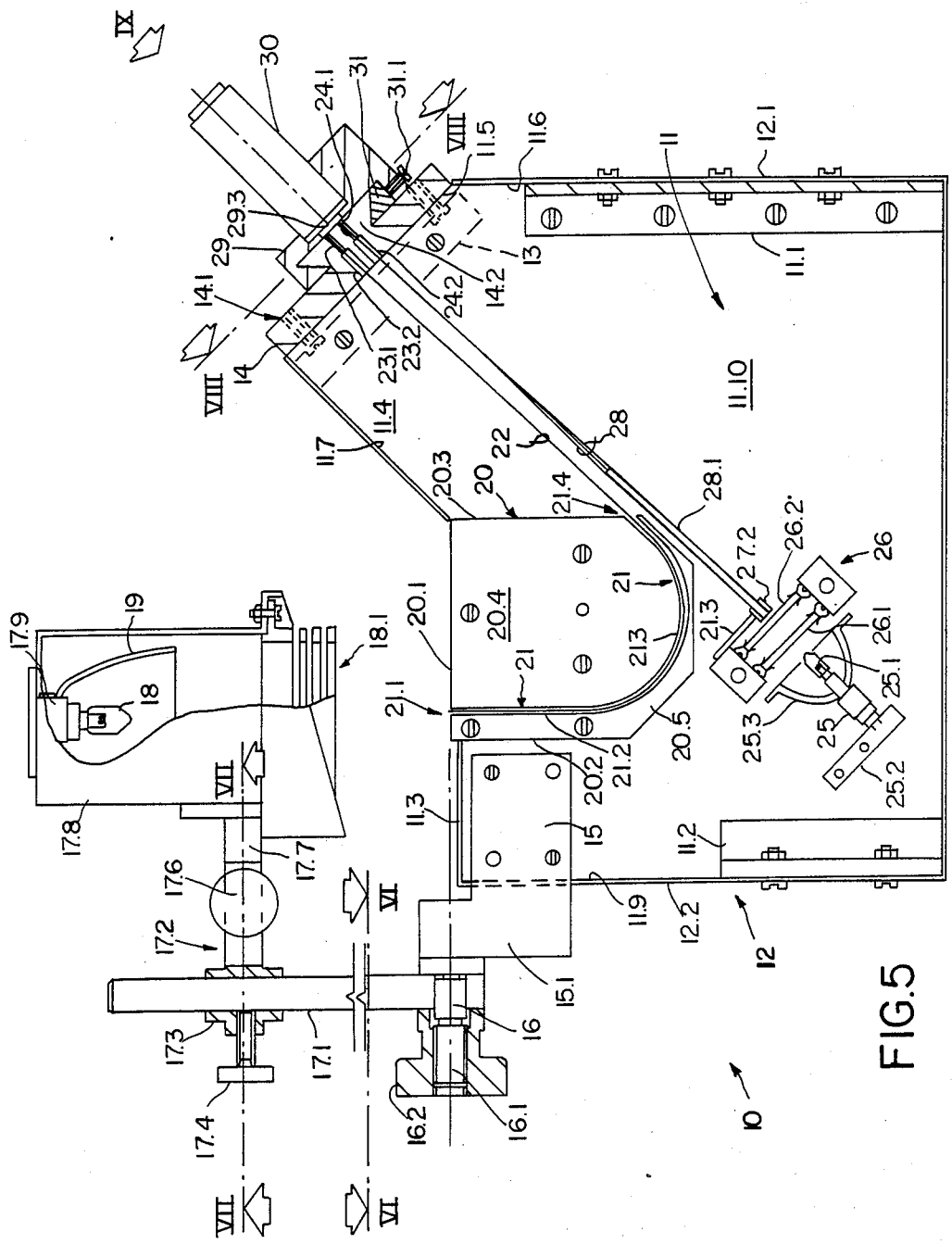
FIG. 5 is a cross-sectional view, on a larger scale, of the illuminator in FIG. 1, according to the line V—V in FIG. 6, with portions in partial cutaway for reasons of clarity of illustration.
Figure 6:
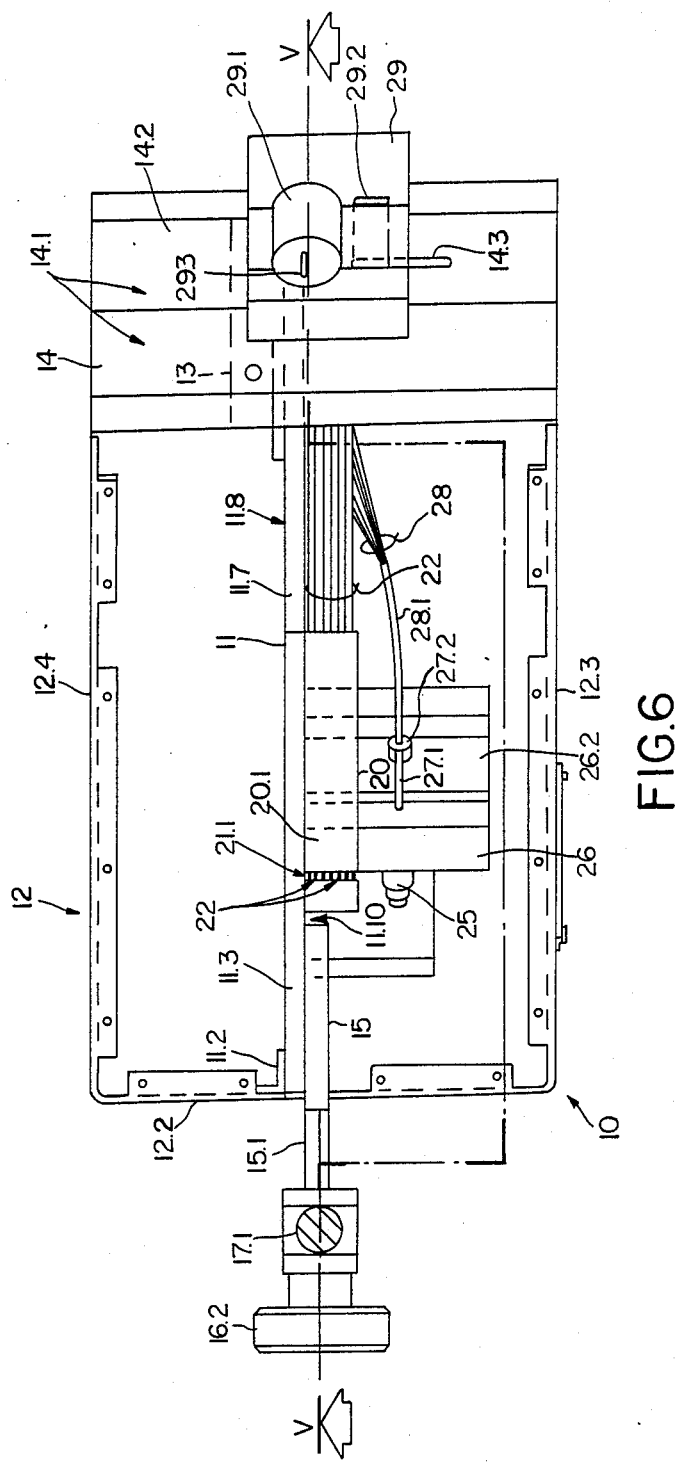
FIG. 6 is a cross-sectional view according to the line VI—VI in FIG. 5, with the lid for the box-shaped housing and spectroscope removed for reasons of clarity of illustration.

The illuminator 10 comprises a sturdy support plate 11, vertical, of metal, e.g. aluminum, having a substantially rectangular body. This support plate 11 is housed for support and protection, fixed inside a box-shaped housing 12 e.g. of sheet metal, by means of pairs of metal angles, 11.1, 11.2, joined to the frontal wall 12.1 and dorsal wall 12.2 of this box-shaped housing 12, e.g. by means of screws. This box-shaped housing 12 forms the stand for the illuminator 10. The support plate 11 is arranged parallel and close to the longitudinal vertical middle plane of the box-shaped housing 12. On the side of the top 11.3 of the plate 11, there extends an integral fin 11.4 complanate to the rectangular body of the plate itself, and having a substantially triangular profile (FIG. 5). One side 11.5 of this fin 11.4 is joined, with an inclination of substantially 45 degrees with respect to the vertical, to the front vertical side 11.6 of the aforesaid plate 11, while the other side 11.7 of this fin is joined to the top side 11.3 of the plate 11, in the proximity of the transversal vertical middle plane of the plate itself. An "L"-shaped metal section 13 is fixed, along one of its sides, e.g. by means of screws, onto the face 11.8 (FIG. 6) of the plate 11 distal from the longitudinal vertical middle plane of the box-shaped housing 12, and with the base face of its open side complanate with respect to the inclined side 11.5 of the fin 11.4 of the aforesaid plate 11. This "L"-shaped section 13 forms a support bracket, upon which there is fixed, e.g. by means of screws, a sturdy metal plate 14, e.g. of aluminum, rectangular, "cantilevered" transversally to the support plate 11 to close the corresponding space between the two side walls 12.3, 12.4, of the box-shaped housing 12. It shall be noted in this connection that the side walls 12.3, 12.4 of the box-shaped housing 12 leave a profile corresponding to the profile for the support plate 11 with the fin 11.4, while the frontal wall 12.1 and the dorsal wall 12.2 of the housing itself have a rectangular perimetrical contour with a height corresponding to the height of the corresponding vertical side, anterior 11.6 or posterior 11.9, of the aforementioned plate 11 which they are right up against. The abovementioned rectangular plate 14 is inclined substantially at 45 degrees with respect to the transversal vertical middle plane of the box-shaped housing 12 and forms the support table, with respect to which there is supported the sliding spectroscope for the illuminator 10, as shall become clearer further on. On its in-view face 14.1, this plate 14 has a projecting integral dovetail slide guide 14.2, substantially in the middle and extended throughout its length.

The support plate 11, in the corner zone delineated by its posterior vertical side 11.9 and top side 11.3 and along its face 11.10 proximal to the longitudinal vertical middle plane of the box-shaped housing 12, carries fixed, e.g. by means of screws, an "L"-shaped support stirrup 15, whose free vertical arm 15.1, extends outside the box-shaped housing 12. This vertical branch 15.1 of the support stirrup 15 comprises an integral joint pin 16 (FIG. 5), having a threaded free extremity 16.1 and with an axis that is horizontal and substantially complanate with respect to the longitudinal vertical middle plane of the box-shaped housing 12. The axis for this pin 16 lies in a horizontal plan slightly overhanging the top side 11.3 of the support plate 11. Upon this pin 16 there is jointed, at one of its corresponding extremity zones, a cylindrical arm 17.1 which can be oscillated around this same pin in a vertical plane transversal with respect to the longitudinal vertical middle plane of the box-shaped housing 12. In order temporarily to stabilize this oscillatable arm 17.1 into the desired position of rotation around the joint pin 16, there is provided a manually tightened cylindrical nut 16.2, employed for screwing onto the threaded free extremity zone 16.1 of the aforementioned pin 16, and having e.g. a knurled lateral surface. The aforesaid oscillatable arm 17.1 in turn carries an orthogonal, sliding clamp arm 17.2. This clamp arm 17.2 is designed for axial sliding onto the oscillatable arm 17.1, and can be oriented in orthogonal planes with respect thereto by means of its sleeve-shaped extremity zone 17.3, having a radial passing setscrew 17.4, which can be manually tightened for the locking of the same sliding arm 17.2 into the desired slide and rotation position with respect to the cylindrical arm 17.1. At its extremity zone opposite from the aforementioned sleeve 17.3, the sliding arm 17.2 is provided with a clamp 17.5 having fixed jaws, which can be elastically brought closer together through the screwing of a suitable screw pin 17.6 with an axis lying in a plane normal to the axis of the arm 17.1 and bearing a head which can be gripped for manual tightening and untightening (FIG. 7). Upon this screw pin 17.6 and between the jaws of the clamp 17.5 there is jointed an "L"-shaped stirrup branch 17.7, the other branch of which carries fixed a substantially cylindrical rigid cap 17.8, e.g. of sheet metal, for housing and protecting a lamp-holder 17.9. The "L"-shaped stirrup 17.7 can accordingly be oscillated, integrally with the cap 17.8, in planes passing through the axis of the cylindrical arm 17.1 and can be adjusted, in a releasable fashion, into the desired oscillation position through screwing of the screw pin 17.6. The lamp-holder 17.9 carries, electrically connected, a white-light incandescent illumination lamp 18, e.g. a halogen lamp. In the aperture of the mouth of the cap 17.8 there is assembled, e.g. by means of screws, a tubular filter-holder 18.1, with circumferential passing grooves for the housing of suitable removable optical filters, including (if necessary) an antiheat filter, not illustrated. The light emitted by the lamp 18 is reflected by means of a non-dichroic, ellipsoidal specular reflector 19, e.g. of aluminum. This lamp 18 is positioned substantially at the first focus of this ellipsoidal reflector 19.

By means of the described arrangement, the lamp 18 is supported outside the box-shaped housing 12, and can be oriented through oscillation in transversal vertical planes with respect to the longitudinal vertical middle plane of this box-shaped housing, and can be brought closer towards or farther away from the box-shaped housing itself.

In the space between the support stirrup 15 and the fin 11.4, on the face 11.10 of the support plate 11 there is fixed, e.g. by means of screws, a "cantilevered" optical-fiber-holder block 20, of metal, e.g. aluminum, substantially parallelepipedal and with transversal edges having a rounded base. The longitudinal vertical middle plane of the box-shaped housing 12 substantially coincides with the plane of longitudinal symmetry of the block 20. This block 20 presents its plane top face 20.1 overhanging with respect to the top side 11.3 of the plate 11 and substantially complanate with the axis of the horizontal pin 16, with respect to a horizontal plane. The height of the block 20 is substantially equal to half the height of the support plate 11, measured with respect to the top side 11.3. In the aforementioned block 20, there is provided a channel seating 21 for housing and retaining seven optical fibers 22, e.g. of silica glass, through an initial section of their length and in an arrangement in which the optical fibers are placed side by side one another. The longitudinal vertical middle plane of the box-shaped housing 12 also substantially coincides with the plane of longitudinal symmetry of the channel seating 21. This channel seating 21 is open, at 21.1, at the top face 20.1 of the block 20, at the level of which there emerge, through the same aperture 21.1, the incoming or receiving extremities of the seven optical fibers 22, arranged there alongside one another in accordance with a transversal vertical plane with respect to the support plate 11. The channel seating 21 extends into the block 20 in a rectilinear preliminary section 21.2, close and substantially parallel with respect to the side 20.2 of the same block proximal to the support stirrup 15, and this merges into an additional section 21.3 having a curvilinear configuration, in the manner of a semicircular bend, to emerge at an aperture 21.4 on the other side 20.3 of the block 20, face to face with respect to the support table 14 for the spectroscope. In this curvilinear-section 21.3 of the channel seating 21 the optical fibers 22 are also housed and maintained in an arrangement in which they are placed side by side one another. In the dovetail slide guide 14.2 of table 14, in a position opposite to the aperture 21.4 of the block 20, there are provided seven through holes, mutually aligned in the longitudinal direction of the guide itself, indicated in their entirety with 23 in FIG. 8 and of which the first through hole, indicated with 23.1, is visible in FIG. 5. The arrangement of the holes 23 is specularly symmetrical with respect to the aforementioned longitudinal vertical middle plane of the box-shaped housing 12. The axes for these holes 23 lie in a plane parallel to the longitudinal vertical middle plane of the aforementioned slide guide 14.2, and which further constitutes a plane of symmetry for the aforesaid aperture 21.4 of the block 20. Each one of the seven optical fibers 22 is fixed, at its terminal extremity zone, distal from the block 20, into one of the aforementioned through holes 23 respectively, e.g. by means of gluing. The terminal extremities of the aforementioned optical fibers 22 emerge at the level of the in-view face 14.1 of the table 14 (at the slide guide 14.2 of the same table), forming the examination plane with respect to a spectroscope-holder slide, as shall become clearer further on. Accordingly, the aforesaid optical fibers 22 are held in a stable fashion, one by one, through form coupling in the channel seating 21 of the block 20, in which the optical fibers extend over a curvilinear course, and are kept outstretched between the aperture 21.4 of this same block 20 and the aforementioned through holes 23, still in a side-by-side arrangement. In order to facilitate the assembly of the optical fibers 22, these through holes 23 open into a common eyelet 23.2 formed on the not-in-view face of the aforementioned table 14. The block 20 is formed in two bodies 20.4, 20.5, facing one another with a free interspace, to define the aforementioned channel seating 21.

The through holes 23 for assembling the terminal extremities of the optical fibers 22 are aligned on one side of the longitudinal vertical middle plane of the slide guide 14.2 of the table 14. In a specularly symmetrical arrangement with respect to these holes 23, with reference to the longitudinal vertical middle plane of the slide guide 14.2, there are provided on the same guide just the same number of through holes, indicated in their entirety with 24 in FIG. 8, and of which the first through hole, indicated with 24.1, is visible in FIG. 5. These holes 24 also emerge in a common eyelet 24.2 formed on the not-in-view face of the aforementioned table 14.

In a position underlying the block 20, a lamp-holder 25 with lamp 25.1, is fixed by means of a base slab 25.2, onto the face 11.10 of the support plate 11, e.g. by means of screws, with its axis substantially parallel with respect to the axes for the aforementioned holes 24 in the support table 14 for the spectroscope. The light emitted by the lamp 25.1, intended to serve as "comparison" light, as shall become clearer further on, is reflected by means of an ellipsoidal, non-dichroic specular reflector 25.3, e.g. of aluminum. This white-light incandescent lamp 25.1, e.g. a halogen lamp, having the same color temperature as the illumination lamp 18, is positioned substantially at the first focus for the aforesaid reflector 25.3. In the course of the beam of light emitted by the lamp 25.1, in front of the abovementioned lamp-holder 25, there is supported, fixed with respect to plate 11, a filter-holder 26 carrying e.g. an antiheat filter 26.1, in addition to a transparent comparison substance 26.2. Downstream from this transparent substance 26.2, in the direction of the flow of light, there is supported, by means of a rigid arm 27.1 fixed to the filter-holder 26, a ferrule 27.2 coaxial with respect to the aforementioned lamp-holder 25. Upon said ferrule 27.2, positioned substantially at the second focus of the ellipsodial reflector 25.3, there is fixed the incoming extremity of a sheaf of seven optical fibers 28 (one central optical fiber and six in a hexagonal arrangement in contact with that central optical fiber), e.g. of silica glass, joined together through an initial section of their length into a flexible sheat 28.1 and fixed to their other extremity, singularized one by one, into one of the holes 24 respectively in the table 14, e.g. through gluing. The optical fibers 28 also emerge at the level of the in-view face of the table 14 (at the slide guide 14.2 of the same table) forming the examination plane with respect to a spectroscope-holder slide, as shall become clearer further on. The optical fibers 22 and 28 are made e.g. of silica glass treated to reduce the absorption in the blue/violet region of the visible spectrum and in the adjacent ultraviolet region. These optical fibers advantageously have a monofiber structure, as illustrated, with a diameter e.g. of 1 mm.

A lid 12.5 is arranged to close the box-shaped housing 12 (FIG. 3). This lid 12.5 has a central slot with respect to which there emerges the top face 20.1 of the block 20, forming, at the aperture 21.1 of the channel seating 21 of the optical fibers 22, the support plane for the substance under examination.

In the slide guide 14.2 of the support table 14 for the spectroscope, there is provided a wide passing eyelet hole 14.3, the longitudinal axis for which is substantially complanate to the axis of the lamp-holder 25, and it is contained in the longitudinal vertical middle plane of the aforementioned slide guide 14.2.

Upon the dovetail slide guide 14.2 there is provided a corresponding spectroscope-holder slide 29, sliding longitudinally with respect to the guide itself and with a substantially circular blind hole 29.1, having an axis normal to the aforesaid guide and provided for the assembly of a spectroscope 30. This slide 29 further has a passing eyelet hole 29.2, the longitudinal axis of which lies substantially in the longitudinal vertical middle plane of the slide guide 14.2. This longitudinal eyelet hole 29.2 displays dimensions significantly smaller than the dimensions for the eyelet hole 14.3 provided in the slide guide 14.2. In the bottom wall of the aforementioned blind hole 29.1 there is formed a through eyelet 29.3 having a longitudinal axis normal with respect to the longitudinal vertical middle plane of the slide guide 14.2. The dimensions for this eyelet 29.3 are such as to include, in pairs upon the in-view surface 14.1 of the slide guide 14.2, forming an examination plane with respect to the slide 29, one hole from the set of holes 23 and one hole from the set of holes 24, for the assembly of the terminal extremities of optical fibers 22 and 28 respectively. In addition, this eyelet 29.3 is of dimensions at least corresponding to the dimensions of the frontal slit of the spectroscope 30. The vertical plane passing through the longitudinal axis of the aforementioned eyelet 29.3 contains the axis of observation through the spectroscope 30. This plane is normal with respect to the vertical planes in which the illumination lamp 18 can be oriented through oscillation. Furthermore, for each positioning of the slide 29 with eyelet 29.3 corresponding to a pair of holes 23, 24, the longitudinal eyelet hole 29.2 for the aforementioned slide always finds itself positioned at the eyelet hole 14.3 in the slide guide 14.2. The beam of residual light passing through these eyelet holes 14.3 and 29.2 and emitted by the lamp 25.1 is used to illuminate the scale 30.1 for the spectroscope 30 (FIGS. 1, 3).

In FIGS. 5 and 10, with 31 there is indicated a gib for recovering the allowances, which can be adjusted by means of a screw 31.1. In FIGS. 1 and 3, with 32 there are indicated the aeration slits formed in the box-shaped housing 12 at the lamp 25.1 accommodated inside that same housing, while with 34 there is indicated a hatch which can be opened to gain access to the zone of the lamp-holder 25 and the filter-holder 26 in the aforementioned box-shaped housing 12.

The electrical means for connecting up and feeding the electrical components in the illuminator 10, known in and of themselves, have not been indicated so as to simplify the illustration.

B. Operation of the Illuminator In Accordance with the Preferred Embodiment.

The illuminator 10 is electrically connected into the network and the lamps 18 and 25.1 are electrically inserted. The substance to be examined is arranged upon the support plane 20.1 at the aperture 21.1 at which the optical fibers 22 emerge. The substance comes into contact or at all events into close proximity with the incoming extremity of one or more optical fibers 22. After having untightened the setscrew 17.4, one axially slides and if necessary one rotates the clamp arm 17.2 with respect to the cylindrical arm 17.1, until one brings the beam of white light emitted by the lamp 18 substantially to coincide with the substance under examination at the second focus of the ellipsoidal reflector 19, at which the beam itself is concentrated. The clamp arm 17.2 is locked into position once again. Depending upon the shape and absorption properties of the substance to be examined, after having unfastened the nut 16.2, one orients the cylindrical arm 17.1 in rotation around the pin 16, e.g. into the oscillated position illustrated in FIG. 1 for illumination from above the substance. Or else into the oscillated position in FIG. 3 for "skimming" illumination of the substance to be examined, with the axis of the beam of light emitted/reflected by the lamp 18/reflector 19 being always directed according to a plane substantially orthogonal with respect to the vertical plane containing the direction of observation through the spectroscope. With "skimming" illumination, in order to increase the flow of light directed to the substance to be examined, one may arrange, as illustrated in FIG. 3, a removable optical reflector 33 upon the support plane 20.1, so as to focus onto the substance to be examined a portion of the flow of light which would otherwise have to be dispersed. This removable reflector 33 has a substantially ellipsoidal profile, and is e.g. made of aluminum. The residual light that has passed through the substance to be examined enters into the incoming extremity of the optical fibers 22 with respect to which the substance itself is in contact or in close proximity. This residual light is transmitted along these optical fibers 22 as far as their terminal extremity on the in-view face 14.1 of the slide guide 14.2 for the table 14, forming an examination surface with respect to the spectroscope-holder slide 29. In the course of this journey, the residual light is homogenized inside these optical fibers 22. Consequently, at the output for each one of these optical fibers 22 there is emitted a beam of residual light having an axis substantially parallel to the direction of observation through the spectroscope 30. At the same time, at the output for the optical fibers 28 there is emitted a comparison light beam having an axis substantially parallel to the direction of observation through the spectroscope 30 and originating from lamp 25.1, helpful for comparative analysis. In order to optimize the spectroscopic observation, the observer verifies which of the optical fibers 22 is transmitting at its terminal extremity, at that particular time and for that particular substance, the residual light best suited to spectroscopic observation, and the observer does this by manually moving forward and backward the substance under examination on the support plane 20.1 at the initial extremities of the aforementioned optical fibers 22. This checking is carried out by observing with the naked eye the terminal extremities of the optical fibers 22 upon the table 14. The optical fiber 22 best suited at that time for spectroscopic observation shall appear at its output to be more luminous and more saturated with the color of the substance under examination. Having singled out that particular optical fiber 22, one causes the slide 29 to slide longitudinally with respect to the guide 14.2, until one brings the frontal slit of the spectroscope 30, positioned facing the eyelet 29.3 of the aforementioned slide, right up over the optical fiber 22 in question in order to carry out the observation. In this position, into the frontal slit of the spectroscope 30 there enters not just the beam of residual light emitted by the chosen optical fiber 22, but also a beam of comparison light emitted by the lamp 25.1 and transmitted by the optical fiber 28, the terminal extremity of which upon the examination plane 14.1 of the slide guide 14.2 turns out to be paired, in the eyelet hole 29.3 of the slide 29, with the terminal extremity of that particular optical fiber 22 chosen by the analyst for spectroscopic observation.

As evidenced by the foregoing considerations, the principal advantages of the illuminator pursuant to the invention are as follows:

The optical fibers for transferring the residual light from the substance under examination to the spectroscope, e.g. consisting of silica glass and having a monofiber structure, with a diameter e.g. of 1 mm, cause the residual light to be homogenized along the distance which they cover, in such a way that the frontal slit of the spectroscope is illuminated in a homogenous fashion, and spectra with patches are accordingly avoided. There is a minimal loss of luminous energy, especially in the blue/violet and ultraviolet region of the spectrum, on account of the material's high transmittance vis-a-vis the light in that particular region of the spectrum. There is also a minimal entry into the spectroscope of parasitical light, i.e. light that has not passed through the substance under examination, even e.g. in the case of small stones or in the case of edges of stones that are highly absorbent in the visible spectrum. Advantageously, these optical fibers consist of silica glass specially treated so as to be the least absorbent possible in the blue/violet region of the visible spectrum and in the neighboring ultraviolet region.

It shall further be noted that a relatively long and curvilinear course for the optical fibers is conductive to the correct homogenization of the light inside the optical fibers.

The small diameter of each optical fiber, in conjunction with the fact that the substance under examination is being supported directly in contact or in close proximity with the incoming extremity of the fiber itself, makes it possible, with the proper regulation of the beam of incident light, for all of the residual light and that alone (involving the entire cross-sectional area of the incoming extremity of the optical fiber) to enter the optical fiber concerned, to be transported thereby to the spectroscope's slit. In this way, it is possible to analyze residual light that is not mixed in with light originating from the lamp that has not passed through the substance under examination.

Moreover, the relatively small diameter of each optical fiber makes it possible to recover all and just the residual light from substances, such as stones, even very small stones: right down to minimal dimensions sufficient to entirely cover the surface of the optical fiber concerned (e.g. having a diameter of 1 mm). At the limit, it is possible to analyze the residual light from a substance, such as a stone, having a diameter of 1 mm.

Pursuant to the invention, these advantages can be achieved with the use of just one optical fiber for transferring the residual light from the substance under examination to the frontal slit of the spectroscope.

Instead of optical fibers having a monofiber structure, it is also possible to use optical fibers having a polyfiber structure (reducing in this case only the effect of homogenizing the light transmitted through the optical fibers themselves).

The ellipsodial shape of the specular reflector for the lamp for illuminating the substance under examination enables the light to be focused directly onto the substance itself. It accordingly makes it possible to dispense with the optical media traditionally utilized between the source of illumination light and the substance under examination (except for a possible antiheat filter), in particular with standard optical fibers (of glass), especially absorbent in the blue/violet region of the spectrum and in part of the ultraviolet region of the spectrum. It also makes it possible to use a low-power lamp, e.g. of 50 W. The same applies to the lamp for emitting white light for comparison, the light beam for which is focused, by means of the pertinent specular reflector, onto the incoming extremity of the optical fibers for transmitting comparison white light, or respectively residual light passed through a known substance. The aforementioned lamp for emitting comparison white light may accordingly be housed inside the box-shaped housing 12 without any need for auxiliary means of forced ventilation.

In addition, since the above-mentioned reflector is of aluminum and non-dichroic, absorptions are eliminated in the visible region and in part of the ultraviolet.

The removable specular reflector with respect to the support plane for the substance under examination, serving as a condenser for light onto the substance itself, enables a further recovery of luminous energy with the attendant possibility of using a low-power lamp.

The external arrangement of the lamp for illuminating the substance under examination makes it possible to dispense with the cooling fan, necessary in known illuminators.

The pairing, with respect to the frontal slit of the observation spectroscope, of the terminal extremity of each optical fiber for transmitting the residual light from the substance under examination to the spectroscope with the terminal extremity of an optical fiber for transmitting the light from a comparison lamp to the same spectroscope, makes it possible to identify faint absorptions otherwise unrecognizable as such and to compare with spectra for known substances.

The direction of the light beam for the substance under examination, being substantially orthogonal with respect to the vertical plane containing the analyst's direction of observation, makes it possible to prevent the analyst from being dazzled in the course of the analysis and of the operations for arranging the substance.

Naturally, numerous variations may be introduced with respect to the foregoing descriptions and illustrations, given solely by way of non-restrictive example, without thereby departing from the scope of the invention and hence from the purview of the present patent right.

Figure 12:
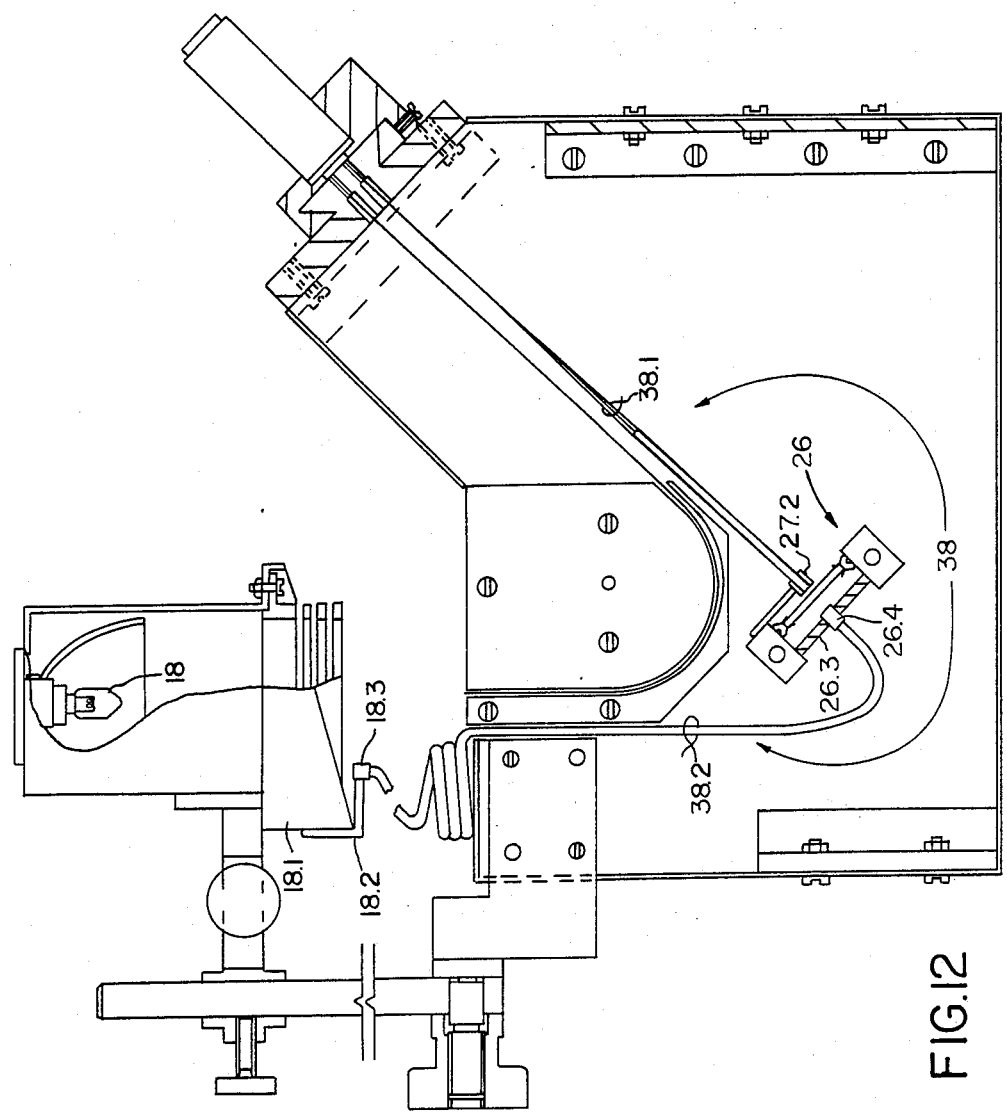

In this way, for example, the lamp for emitting comparison white light may be omitted, by using just the white light emitted by the same lamp for illuminating the substance under examination also as comparison white light, sent to the pertinent optical fibers, and for illuminating the scale on the spectroscope. In FIG. 12 it has been schematically indicated how this can be done, for example by the addition of another branch 38.2 of optical fibers. More particularly, as will be seen from this schematic representation the bundle 38 of optical fibers for transmitting comparison white light or residual light through a known substance comprises two branches, a branch 38.1 similar to the optical fibers 28 according to FIGS. 1, 5, 6 and the aforementioned branch 38.2. In addition, the support table for the observation spectroscope may have, instead of a rectilinear-trending examination plane, a curvilinear examination plane with respect to which the same spectroscope is operationally positioned. At the same time, the support plane for the substance under examination may be formed by a plate supported with respect to the illuminator stand, instead of by the top face of the optical-fiber-holder block.

I claim:

1. Illuminator for the spectroscopic observation of minerals, gems, etc., in which a substance under examination is illuminated by means of a source of white light, said illuminator comprising at least one optical fiber (22) for transmitting the residual illumination light, passed through the substance under examination, to an observation spectroscope, one of the ends of each said optical fibers (22) being disposed in direct contact or in close proximity with the substance under examination in the illuminator, in such a way that the optical fiber (22) receives the residual illumination light passed through the substance under examination at said one end and transmits it to said observation spectroscope.

2. Illuminator as per claim 1, in which the substance under examination is mounted on a support, and wherein said one end of each optical fiber (22) is disposed in the plane (20) of said support.

3. Illuminator as per claim 2, wherein said spectroscope has a frontal slit and wherein the other end of each optical fiber (22) for transmitting the residual illumination light passed through the substance under examination, is disposed at an examination plane (14.1) with respect to which said observation spectroscope (30) is arranged to be positioned facing the last-mentioned end of the optical fiber (22), in such a way that said optical fiber (22) emits through said end a beam of residual light passed through the substance under examination straight to said frontal slit substantially in a direction parallel to the direction of observation through the spectroscope itself.

4. Illuminator as per claim 3, which comprises multiple optical fibers (22) for transmitting the residual illumination light passed through the substance under examination, to their respective ends at said examination plane (14.1), and wherein a spectroscope-holder (29) is supported for sliding movement on said illuminator, with respect to said examination plane, means (14, 14.2) being provided for supporting and guiding said spectroscope-holder, in such a way that said frontal slit of the spectroscope (30) housed in the sliding spectroscope-holder (29) can be selectively aligned with a corresponding one of said last-mentioned ends of each optical fiber (22) so as to receive just the beam of residual light, passed through the substance under examination, emitted by said end of the optical fiber (22), with the first-mentioned opposite ends of said optical fibers (22) being disposed at the support plane (20.1) for the substance under examination in the illuminator.

5. Illuminator as per claim 4, wherein each optical fiber (22) for transmitting the residual illumination light passed through the substance under examination, has a curvilinear configuration for at least one section of its length, in such a way that the residual illumination light is homogenized in its passage through said optical fiber (22).

6. Illuminator as per claim 5, comprising at least one optical fiber (28) for the transmission to said observation spectroscope (30) of comparison white light, or of residual light passed through a known substance, independent of each optical fiber (22) for transmitting the residual illumination light passed through the substance under examination, in such a way as to enable the observer through the spectroscope (30) to make a direct comparison between the residual illumination light passed through the substance under examination, and the spectrum for the comparison white light, or the spectrum for said known substance.

7. Illuminator as per claim 6, wherein one of the ends of each optical fiber (28) for transmitting comparison white light, or residual light passed through said known substance, is disposed at an examination plane (14.1) with respect to which the observation spectroscope (30) is arranged to be positioned in front of said end of the optical fiber (28), in such a way that said optical fiber (28) emits through said end a beam of white comparison light, or a beam of residual light passed through said known substance, straight to the frontal slit of said spectroscope (30) substantially in the direction of observation through the spectroscope itself, with said beam of light being directed along an axis substantially parallel to the axis of the beam of light emitted through the end at the examination plane (14.1) of each optical fiber (22) for transmitting the residual illumination light passed through the substance under examination, with the opposite end of each optical fiber (28) for transmitting comparison white light, or of residual light passed through said known substance, being arranged to receive and transmit the comparison white light, or the residual light passed through said known substance.

8. Illuminator as per claim 7, comprising multiple optical fibers (28) for transmitting comparison white light, or residual light passed through said known substance, to ends arranged at the examination plane (14.1) in such a way that the frontal slit of the spectroscope (30) mounted on the sliding spectroscope-holder (29) may be selectively aligned with a corresponding end of each optical fiber (28) so as to receive just the beam of comparison white light, or of residual light passed through said known substance, emitted by said end of the optical fiber (28).

9. Illuminator as per claim 8, wherein the respective ends of the optical fibers (22) for transmitting the residual illumination light passed through the substance under examination, and the ends of the optical fibers (28) for transmitting the comparison white light, or the residual light passed through said known substance, arranged at the examination plane, are paired two by two, in adjacent relationship and with axes substantially parallel to one another, which are directed to the frontal slit of the spectroscope (30), in such a way that through the spectroscope, for every operational positioning thereof with respect to the corresponding paired ends of the optical fibers (22, 28), the observer can see in turn two contiguous spectra simultaneously, of which one spectrum is for the substance under examination and the other spectrum is for the comparison white light, or for said known substance.

10. Illuminator as per claim 2, wherein said illuminator has a housing (12) and wherein said source of white light (18) for illuminating the substance under examination is supported outside the illuminator housing (12).

11. Illuminator as per claim 10, wherein the source of white light (18) is supported in an oscillatable fashion with respect to the illuminator housing (12) in vertical planes substantially orthogonal with respect to the vertical plane containing the direction of observation through the spectroscope (30), and wherein there is provided an optical reflector (19) for reflecting the light emitted by said source (18), so as to enable the optimal operational positioning of said light source (18) with respect to the substance under examination, and to keep the observer from being dazzled.

12. Illuminator as per claim 10, wherein means are provided for adjusting the source of white light (18) in such a way as to be brought closer towards or farther away from said illuminator housing (12).

13. Illuminator as per claim 2, wherein the white light source (18) is arranged substantially at the first focus of an ellipsoidal optical reflector (19), the second focus of which is adjustable substantially to fall in the support plane (20.1) for the substance under examination in the illuminator.

14. Illuminator as per claim 13, wherein the optical reflector (19) is of a non-transparent reflecting material.

15. Illuminator as per claim 13, wherein in front of the source of white light (18) there is supported a filter-holder (18.1) for removably housing optical filters, for intercepting the beam of light emitted by said light source and reflected by the optical reflector (19) associated with said light source.

16. Illuminator as per claim 6, wherein the optical fibers for transmitting comparison white light, or residual light passed through said known substance, are arranged to receive and transmit the white light emitted by the source of white light for illuminating the substance under examination.

17. Illuminator as per claim 6, wherein the optical fibers (28) for transmitting comparison white light, or residual light passed through said known substance, are arranged to receive and transmit the light emitted by a source of comparison white light (25.1) other than the source of white light (18) for illuminating the substance under examination.

18. Illuminator as per claim 17, wherein the source of white light (18) for illuminating the substance under examination and the source of comparison white light (25.1) have the same color temperature.

19. Illuminator as per claim 17, wherein the source of comparison white light is arranged substantially at the first focus of an ellipsoidal optical reflector (25.3).

20. Illuminator as per claim 19, wherein the lastmentioned optical reflector (25.3) is made of non-transparent reflecting material.

21. Illuminator as per claim 19, wherein substantially at the second focus of the lastmentioned ellipsoidal optical reflector (25.3) there are arranged the ends, joined together into a sheaf, of the optical fibers (28) for transmitting comparison white light, or residual light passed through said known substance, in such a way as to receive and transmit the light emitted/reflected by the light source (25.1) and the optical reflector (25.3), the lastmentioned light source (25.1) being adjustable.

22. Illuminator as per claim 17, wherein in the path of the beam of comparison white light there is arranged a filter-holder (26) for removably housing optical filters, downstream from which, in the direction the flow of the corresponding beam of light, there is arranged the end, at which the light from said beam is received, of each optical fiber (28) for transmitting comparison white light, or residual light passed through said known substance.

23. Illuminator as per claim 22, wherein in the last-mentioned filter-holder (26) there is removably housed a transparent known substance, for comparison.

24. Illuminator as per claim 1, wherein said spectroscope has a scale and wherein the light emitted by the aforementioned source of white light for illuminating the substance under examination is arranged to also illuminate said scale.

25. Illuminator as per claim 17, wherein said spectroscope has a scale and wherein the light emitted by the source of comparison white light (25.1) is arranged to also illuminate said scale.

26. Illuminator as per claim 25, wherein the light emitted by the source of comparison white light (25.1) and arranged to illuminate the scale for the spectroscope (30) passes through eyelet holes (14.3, 29.2) provided respectively in said means of support and guidance (14, 14.2) and in said spectroscope-holder (29), which eyelet holes (14.3, 29.2), for every operational positioning of the spectroscope (30) housed in said spectroscope-holder (29) sliding with respect to said means of support and guidance (14, 14.2), always define among themselves a free passage for the light emitted by the source of comparison light (25.1).

27. Illuminator as per claim 2, comprising a removable optical reflector (33), arranged to be selectively positioned on the support plane (20.1) for the substance under examination in the illuminator, so as to focus onto the substance itself a portion of the flow of light emitted by the source of white light, which would otherwise be dispersed.

28. Illuminator as per claim 1, wherein said spectroscope has a frontal slit and wherein each optical fiber (22,28) has a monofiber structure, thereby causing the residual light to be homogenized along the distance which they cover, in such a way that the frontal slit of the spectroscope is illuminated in a homogeneous fashion, and spectra with patches are avoided.

29. Illuminator as per claim 2, wherein each optical fiber (22, 28) has a polyfiber structure.

30. Illuminator as per claim 1, wherein each optical fiber (22, 28) is of silica glass.

31. Illuminator as per claim 30, in which each optical fiber (22, 28) is of silica glass treated to reduce absorption in the blue/violet region of the visible spectrum and in the neighboring ultraviolet region.

32. Illuminator as per claim 5, comprising multiple optical fibers (22) for transmitting the residual light passed through the substance under examination, said fibers being accommodated inside a box-shaped housing (12), and being held through an initial section of their length, side by side in a channel seating (21), provided in a fiber-holder block (20) and terminating, at one end (at 21.1) at the top face of said block (20), in the support plane for the substance under examination, said fibers, upon emerging (at 21.4) from said channel seating (21) terminating at the other end at a table (14) upon which there is slidingly supported the spectroscope, and wherein on said table (14) there are provided multiple through holes (23), in a number corresponding to the number of the optical fibers (22) into which through holes there are fixed the respective opposite ends of said optical fibers (22), said fibers emerging, through said holes (23), at the level of the in-view face of the table (14) which latter forms said examination plane (14.1) of the spectroscope-holder slide (29), said slide sliding along a longitudinal slide guide (14.2), integral with said table (14) and carrying said spectroscope (30), said through holes (23) being aligned among themselves in the direction of sliding for the slide (29) with respect to the guide (14.2).

33. Illuminator as per claim 32, wherein in said table (14) there are provided second multiple through holes (24), aligned among themselves, parallel in arrangement and equal in number to the firstmentioned through holes (23), and constituting seatings for accommodating the respective ends of the optical fibers (28) through which there is emitted to the spectroscope (30) the comparison white light, or the residual light passed through said known substance.

34. Illuminator as per claim 32, wherein the optical fibers (22) for transmitting the residual light, passed through the substance under examination, are arranged side by side among themselves, in the channel seating (21) at the level of the top face of said block (22), in a vertical plane substantially orthogonal to the vertical plane containing the direction of observation through the spectroscope (30), and wherein there are provided means for adjusting the source of white light (18) in such a way that the axis of the beam of white light emitted by said source is contained in this same substantially orthogonal plane.

35. Illuminator as per claim 1, wherein the source of white light consists of a low-power incandescent lamp.

36. Illuminator as per claim 17, wherein the aforementioned source of comparison white light (25.1) consists of a low-power incandescent lamp.

37. Illuminator as per claim 36, wherein said illuminator has a housing (12) and wherein said source of comparison white light (25.1) is located inside said housing (12).

* * * * *